United States Patent [19]

Zissimopoulos

[11] 4,185,759

[45] Jan. 29, 1980

[54] FLUID-FLOW LIMITING APPARATUS FOR USE WITH INTRAVENOUS-SOLUTION ADMINISTERING EQUIPMENT

[75] Inventor: Nick Zissimopoulos, Schaumburg, Ill.

[73] Assignee: Baxter Travenol Laboratories, Inc., Deerfield, Ill.

[21] Appl. No.: 878,970

[22] Filed: Feb. 17, 1978

[51] Int. Cl.² .............................................. A61M 5/14
[52] U.S. Cl. ................................. 222/450; 222/504; 251/65; 335/179; 335/234; 222/180
[58] Field of Search .............. 222/211, 180, 213, 214, 222/450, 451, 452, 445, 449, 504; 335/79, 179, 234, 266, 268; 251/65

[56] References Cited

U.S. PATENT DOCUMENTS

| 2,673,011 | 3/1954 | Rood et al. | 222/450 X |
| 4,121,584 | 10/1978 | Turner et al. | 222/450 X |

*Primary Examiner*—David A. Scherbel
*Attorney, Agent, or Firm*—Paul C. Flattery; John P. Kirby, Jr.; Garrettson Ellis

[57] ABSTRACT

Improvements in infusion controlling apparatus used in limiting the flow rate of an intravenous solution to a patient. The improvements provide coarse and fine orientations of a casette through which the solution passes relative to a controller which valves the casette's inlet and outlet to provide measured volumes of fluid. The coarse alignment device includes spaced apart metal sections which grasp onto the casette and move it towards the controller's valving members. As the casette reaches the valving members, protuberances on the controller fit into indentations on the casette, as the fine adjustment. The indentations into which the protuberances fit form part of the casette's base section of plastic notwithstanding the location of a cover slip between these two items. The valving members couple to a rocker arm which pivots about a point located at its middle and has magnetic poles at its ends. The rocker arm's pivot point over the center leg of an E-frame electromagnet allows the arm to rotate between two orientations in which one of its magnetic poles contacts a side leg of the E-frame electromagnet. Current passing through a coil located on the center leg of the electromagnet moves the rocker arm between these positions, depending upon the current's direction. With no current in the coil, the arm's magnets and the E-frame provide a bistable magnetic device in which the rocker arm forces one of the valving members to close either the casette's inlet or its outlet. This prevents the uncontrolled passage of fluid through the casette to the patient.

46 Claims, 10 Drawing Figures

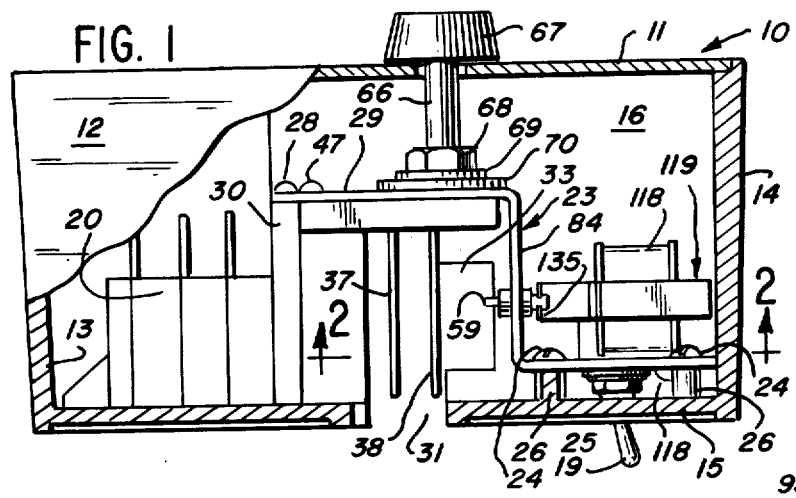
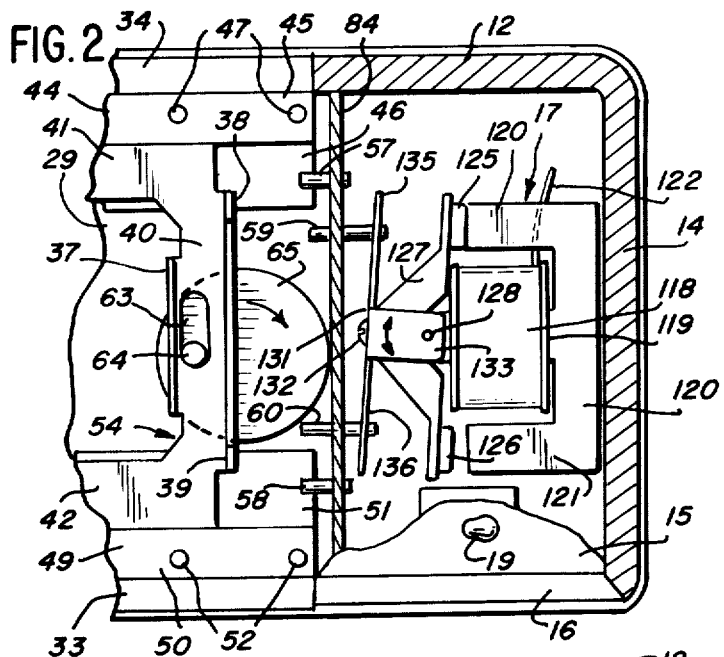
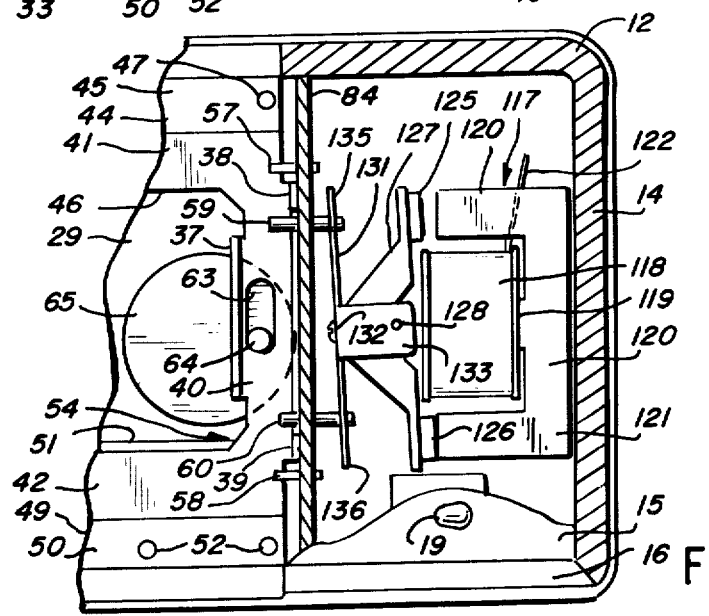
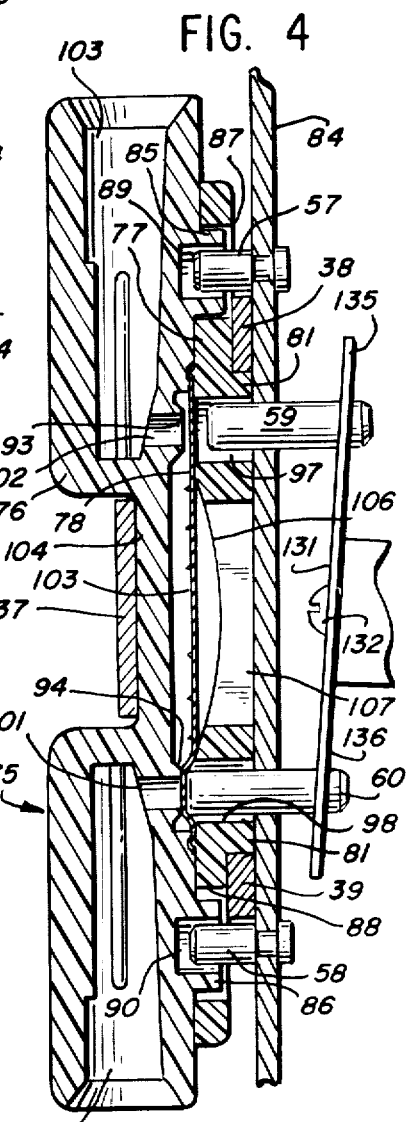
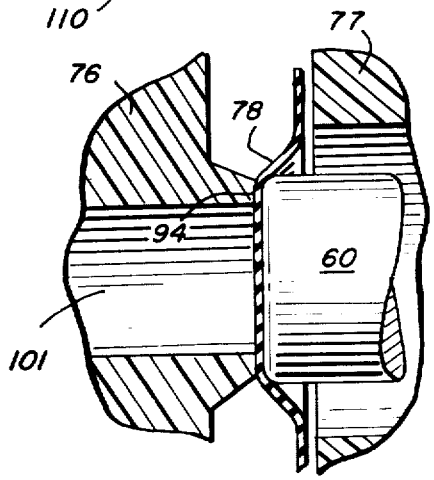

FLUID-FLOW LIMITING APPARATUS FOR USE WITH INTRAVENOUS-SOLUTION ADMINISTERING EQUIPMENT

CROSS-REFERENCES TO RELATED APPLICATIONS

The controller discussed in the subject application may make use of the Z-shaped bracket shown in the design patent application of Nick Zissimopoulous entitled "CASETTE HOLDER AND TRANSPORTER IN A FLUID FLOW LIMITING DEVICE," U.S. Application Ser. No. 878,965, filed Feb. 17, 1978, now abandoned. It may also utilize the electronic circuitry of the pending patent application "DIGITAL ELECTRONICS AND CASETTE SIZE FOR INTRAVENOUS FLUID-FLOW LIMITING EQUIPMENT" of Vincent L. Knigge and Norman Shim, Ser. No. 878,846, filed Feb. 17, 1978; the electromagnetic device of the pending patent application "LOW CURRENT E-FRAME ELECTROMAGNET WITH A PERMANENT MAGNET ARMATURE FOR AN I.V. VALVING CONTROLLER" of Orest Hrynewycz, U.S. application Ser. No. 878,650, filed Feb. 17, 1978; and either of the electromagnet shapes displayed in the design patent applications "E-FRAME ELECTROMAGNET HAVING A PERMANENT MAGNET ROCKER-ARM ARMATURE" of Orest Hrynewycz, U.S. application Ser. No. 878,649, filed Feb. 17, 1978 and now abandoned; and "E-FRAME ELECTROMAGNET HAVING PERMANENT MAGNETS ATTACHED TO A ROCKER-ARM ARMATURE" of Nick Zissimopoulous, application Ser. No. 878,832, filed Feb. 17, 1978 and now abandoned. In addition to aspects to the above applications, the casette in the subject application may utilize a structure including the elastomeric membrane discussed in the pending patent application "CASETTE FOR USE WITH AN I.V. INFUSION CONTROLLER" of Scott T. Garrett, Lee K. Kulle, and William L. Rudzena, application Ser. No. 878,966, filed Feb. 17, 1978; the valving configurations of the pending patent application "NON-CRITICALLY ALIGNED VALVING DEVICES FOR FLOW RATE LIMITING CASETTE USED IN INTRAVENOUS SOLUTION ADMINISTERING EQUIPMENT" of Scott T. Garrett, Thurman S. Jess, Vincent L. Knigge, Lee K. Kulle, William L. Rudzena and Nick Zissimopoulous, U.S. application Ser. No. 878,847 filed Feb. 17, 1978; and the shape shown in the design patent application "VALVABLE CASETTE" of Lee K. Kulle and William L. Redzena, Ser. No. 878,962, filed Feb. 17, 1978 and now abandoned. All of these referenced applications have the same filing date as the subject application.

BACKGROUND

In the administration of an intravenous solution, the control of its flow rate to the patient represents a critically important task. Allowed to become excessive, the intravenous solution results in the thinning of the patient's blood in a portion of his vascular system. Tissues depending upon the nutrients and biochemicals entrained in the blood can suffer serious consequences upon the arrival of blood overly diluted with the administered solution.

In U.S. patent application Ser. No. 732,946, R. Scott Turner et al. now U.S. Pat. No. 4,121,584, provides a significant advance in maintaining the flow rate of an intravenous solution at a safe level. One component of Turner et al.'s apparatus takes the form of a metering unit which constitutes part of the flow path followed by the I.V. solution. The metering unit has a metering chamber with a known volume. It also has an inlet and an outlet with a valving device associated with each. Since the solution contacts the metering unit as it flows through it, each unit finds use with a single administering set and is discarded with it.

As the other component of their equipment, Turner et al. provide a controller for sequentially opening and closing the inlet and outlet valves in the metering unit. When the inlet opens, the metering chamber then ingests a predetermined amount of the intravenous solution. The controller then closes the inlet and opens the outlet. This permits the known volume of fluid to flow to the patient. The controller subsequently shuts the outlet and repeats the cycle at a frequency that will deliver the appropriate amount of solution. The metering unit and the controller have minimal weight and may receive support simply from their connection to the intravenous administering set. Since the controller merely opens and closes two valves, it requires minimal electricity and may operate from the current supplied by a battery.

Scott F. Garrett et al., in the patent application "Casette for Use with I.V. Infusion Controller," referenced above, introduce drastic improvements into a casette included as part of the flow path of the intravenous administering equipment. They utilize a section of elastomeric stretchable membrane to form part of a metering chamber having a predetermined volume. The membrane also constitutes part of the inlet and the outlet which passes the fluid into and out of the metering chamber.

A base section of plastic also forms part of the inlet, the outlet, and the metering chamber. A cover slip of plastic then sandwiches the membrane between it and the base piece of plastic. It also limits the expansion of the elastomeric membrane to provide a metering chamber of a known volume. The controller in Garrett et al.'s apparatus need only deform the elastomeric membrane until it makes appropriate contact with the valve seat formed in the base section of plastic.

Providing further improvements to the controller as well as the casette portend the close cooperation of the two in maintaining a safe flow rate of solution to the patient. It can also provide a safeguard even against the slight possibility of a malfunction occurring in the controller.

SUMMARY

A casette typically has a metering means or chamber which holds a predetermined volume of fluid. A closable inlet and a similarly closable outlet remain in fluid communication with the metering chamber. They respectively permit the flow of a flow into and out of the metering chamber.

To operate the casette, the controller has an inlet-controlling means which can close the inlet. Similarly, an outlet-controlling means accomplishes the same task for the outlet from the metering chamber in the casette.

For the controller to properly operate the inlet and the outlet, it must have a predictable location relative to the casette. To provide the appropriate placement, a first positioning means orients the inlet and the outlet on the casette relative to the inlet-controlling and the outlet-controlling means on the controller, respectively. This assures that the action of the controller will, in fact, close and open the appropriate valve, when required, to permit the desired flow rate of solution to a patient.

A second positioning means, independent of the first, may assist in achieving the orientation provided by the latter. Specifically, it should orient the casette relative to the first positioning means itself. With the casette properly located relative to the first positioning means, the casette and the controller may, through the intervenion of the first positioning means, connect together. They, thus, provide proper control of the inlet and the outlet to the metering chamber.

In the casette, a section of substantially rigid material, such as plastic, typically constitutes at least part of the metering chamber. The inlet and the outlet may each include a section of flexible material held between this rigid section and another section of substantially rigid material.

To close the inlet and the outlet, when required, the controller includes a movable rigid member for each. The controller also possesses a moving means which can propel the inlet's movable member through an opening in the additional section of plastic lying in the region of the inlet. The member then pushes the flexible material in the egion of the inlet toward the section of plastic which forms part of the inlet, the outlet, and the metering chamber. The force exerted by the inlet's movable member causes the flexible material to change its shape and close off the inlet. The controller similarily moves the outlet's movable member to close off that opening.

The section of rigid plastic through which the members move, of course, lies closer to the controller's members when the casette sits in its proper position in the controller. This portion of the casette could most conveniently assist in orienting the casette's inlet and outlet relative to the movable members. However, the valve seats for the movable valving members constitute part of the plastic lying on the opposite side of the flexible material. The required orientation, thus, occurs between the valve seats on this piece of plastic and the movable members.

Notwithstanding the intervention of the additional section of plastic over the inlet and the outlet, the positioning means which orients them relative to the movable valve members should couple to the section of plastic having the valve seats. Using that section of plastic to locate the controller and the casette relative to each other directly orients the components that must cooperate to provide the proper valving for the casette.

The controller may also include a transporting device for the casette. It should assist in the functioning of that positioning means which orients the inlet and the outlet of the metering chamber to the inlet- and outlet-controlling means on the casette. The transporter moves the casette between two positions relative to the controller. In one of the positions, the casette lies closer to the inlet- and the outlet-controlling means than in the other.

To assure the retention of the proper orientation once achieved, a locking device may couple to the transporter to prevent any change in position. When it holds the casette in the position closest to the inlet- and outlet-controlling means, the locking device selectively prevents movement of the casette away from it. It does so notwithstanding the application to the casette of a linear force in the direction that the casette moves when travelling away from the inlet- and the outlet-controlling means. When required, of course, the locking device will allow the transporter to disengage the casette from the controller.

The controller also includes an actuating device which can selectively move the inlet's movable member and the outlet's movable member to the positions where they can close off their respective openings. The actuating device moves the members in the proper sequence to allow a predetermined number of measured volumes to flow to the patient from the metering chamber.

Naturally, the actuating device may, on occasion, become nonfunctional. This may result from an insufficient supply of current from a weak battery, for example. In that eventuality, the actuating device may also possess bistable magnetic means for moving either the inlet's movable member into a position where it closes the inlet or the outlet's member to where it closes the outlet. This bistable device assures that at least one of the valves in the casette will remain closed should be controller become nonfunctional. The closing of one valve precludes any flow of fluid to the patient and, thus, prevents any damaging overly large concentration of intravenous solution in the patient's blood stream.

The magnetic operation of the bistable device eliminates the need for mechanical components to accomplish the same task and which themselves can malfunction or wear out and, thus, fail to perform when needed. Moreover, where the actuating device can utilize an electromagnetic operating on electric current, its components may include those required for the bistable magnetic device. In operation, the electomagnet may move the valve members according to the dictates of the controller. When nonfunctioning, the same components become the bistable magnetic device which assures the closure of at least one valve.

To align a casette in the controller, the latter may include an alignment block having a section of substantially rigid material. An attaching means, coupled to this section of material, affixes it to a substantially flat plate having an opening through it. The plate, of course, provides structural support for the moving means which supplies the motive power to the inlet and the outlet valving members. Typically, this takes the form of an electromagnet affixed to the plate.

The plate includes an opening through which pass the two valving members. The members generally have the form of elongated rods. The controller's mechanism should usually remain isolated from the surrounding environment. This protects it from dirt and moisture which could deleteriously affect its performance. Consequently, the section of rigid material should attach to the plate where it can cover substantially all of the plate's opening. It cannot completely cover the opening since the valving members must still pass through it.

A guide then couples to the section of rigid material and should, also, have at least one opening through it. This opening typically allows for the passage of a valving member. In most cases, the controller has two valving members. In this instance, the section of material will, accordingly, also possess two openings. The valving members, in their shape of elongated members, may pass through the openings to operate the casette's valves.

The same section of material may also then include an alignment device coupled to it. This orients an object relative to the guide which controls the positioning of the valving members. Specifically, the guide serves to orient a casette relative to it and, thus, the controller of which it forms part.

Generally, the section of rigid material, the guide, and the alignment device should constitute a single integral block of material. The alignment device may then take the form of protuberances or pins extending from the section of material. They function by fitting tightly into indentations in the casette.

The guide through the section of material has a predetermined position relative to the alignment protuberances. The latter couple directly to the casette. They, thus, do not require installation on the plate of material separate from the guide. Thus, the same component on the controller that aligns the casette also guides the valving members relative to the casette itself.

BRIEF DESCRIPTION OF THE FIGURES

FIG. 1 has a top plan view, partly in cross section, of a controller which operates in conjunction with a casette to provide an upper limit on the flow rate of an intravenous solution to a patient.

FIG. 2 gives a cross-sectional view along the line 2—2 of the controller of FIG. 1 showing the coarse aligning device of the controller in the position in which it receives a casette.

FIG. 3 provides a view similar to that of FIG. 2 but with the coarse aligning device occupying the location where it holds a casette in its operational position in the controller.

FIG. 4 portrays, in an enlarged view, the coarse aligning device of FIG. 3 holding a casette in its operational position with the fine aligning device locating the movable valve members of the controller relative to the valve seats of the casette.

FIG. 5 gives an enlarged view of the outlet valve member of FIG. 4 placing an elastomeric membrane of the casette in contact with the outlet valve seat to close the outlet port.

DETAILED DESCRIPTION

Figure 6:
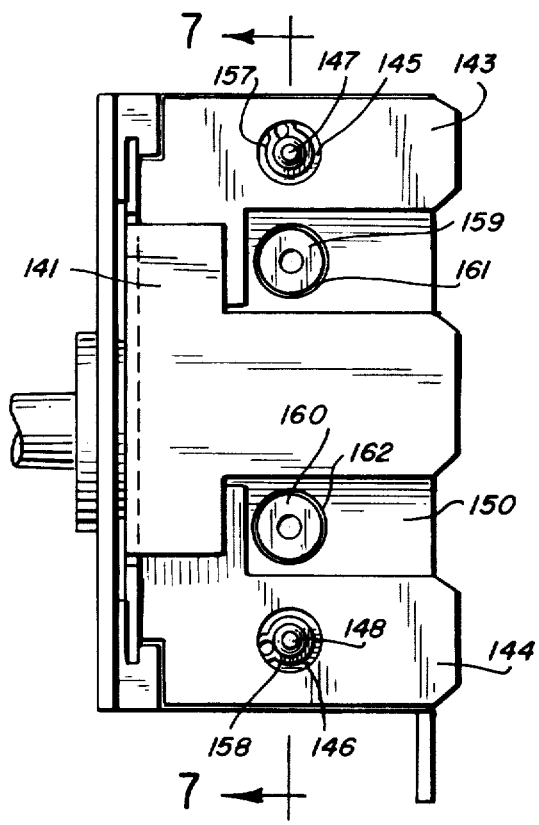
FIG. 6 gives a side elevational view of a structural member holding and aligning a casette in a controller.

The controller 10 of FIG. 1 includes the back panel 11 attached to its casing which consists of the top 12, the sides 13 and 14, the front 15, and the bottom 16. At the front 15 appear the on-off switch 19 and a weak-battery indicator and rate-selection switches which the figure does not show. However, the cover 20 for the rotary selection switches appears behind the front panel 15.

Behind the front panel 15 appears a Z-shaped metal bracket 23. The screws 24 hold the front leg 25 of the Z bracket 23 to the front panel, receiving the assistance of the posts 26 in this task. The screw 28, along with an additional screw beneath it, similarly holds the back leg 29 of the Z bracket 23 to the front panel 15. The post 30 extends from the front panel 15 to the screw 28 to provide an attachment for the latter to the former.

The front panel 15 of the controller 10 has the opening 31 into which can fit a casette. The casette generally has a greater height than does the controller. Moreover, the connections leading to and from the casette extend out of the controller's top and bottom, respectively. Accordingly, an opening 33 in the bottom 16 and a similar opening 34 in the top 12 (seen in FIG. 2) allow for the insertion of the casette into the controller 10 through the front panel 15. As shown in FIG. 1, the opening 33 in the bottom panel 16 has a shape of an inverted "L." The lateral leg of the L-shaped opening permits the movement of the casette from the left to the right. The opening 34 in the top panel 12 has the same shape as the bottom panel's opening 33.

As the casette enters the controller 10 through the front panel 15, it snugly fits between the metal plate 37 and the upper arm 38. As shown in FIG. 2, the lower arm 39 sits below the upper arm 38 and also serves to orient the casette. Moreover, as discussed below with regards to FIG. 4, the two arms 38 and 39 fit snugly around a protuberance on the casette to orient the latter in a vertical direction.

The plate 37 and the arms 38 and 39 form part of a single metal holder. They connect together through the back piece 40 which also has the upper leg 41 and the bottom leg 42. The top of the upper leg 41 sits inside of a groove provided in the upper track 44. As seen in FIG. 2, the track 44 has the thick, short section 45 which sits in front of the upper leg 41. The screws 47 retain the upper track 42 to the back leg 29 of the Z bracket 23.

Similarily, the lower leg 42 sits in a groove formed in the lower track 49. Similar to the upper track 44, the lower track 49 includes the short thick section 50 which sits in front of the lower leg 42. Its thin, long section 51 sits behind the lower leg 42. The screws 52 attach the lower track 49 to the back leg 29 of the Z bracket 23.

The grooves in the tracks 44 and 49 allow the upper and lower legs 41 and 42 to slide to the left and right in FIGS. 1 to 3. Since the legs 41 and 42 must slide to the right and left in the tracks 44 and 49, they should encounter the minimum possible resistance as they do so. Correspondingly, the tracks 44 and 49 may assist this objective by having a composition of a low-friction material such as Teflon ® (manufactured by E. I. du Pont de Nemours & Co., Wilmington, Del.

The legs 41 and 42 move laterally, as does the entire metal holder 54 which includes the legs 41 and 42, the back piece 40, the plate 37 and the arms 38 and 39. When the metal holder 54 occupies its leftward position shown in FIGS. 1 and 2, it allows for the insertion of a casette between the plate 37 and the arms 38 and 39. When the metal holder 54 has moved furthest to the right as in FIG. 3, it places a casette in the position where the controller 10 may open and close the casette's valves.

Furthermore, with the holder 54 in the position of FIG. 3, a casette cannot move towards the front or the rear of the controller 10. The shape of the openings 33 and 34 in the bottom 15 and the top 11, respectively, prohibits this latter type of motion. Preventing the casette from moving forward or backward has particular importance when the casette occupies the position that the holder 54 in FIG. 3 would place it. There, the casette would engage the alignment pins 57 and 58 as well as the inlet valve member 59 and the outlet valve member 60. Moving the casette forward and back while engaged with these items could damage the casette and possibly the components of the controller.

Where the holder 54 occupies the position of FIG. 2 and retains a casette, neither the alignment pins 57 and 58 nor the valve members 59 and 60 can engage the casette. However, the openings in the casette which engage these components fall on straight lines passing through the components' individual centers. Moreover, each of the valve members moves along the same line that leads to the appropriate opening in the casette.

To provide its motion to the right and left, the metal holder 54 has the slotted opening 63 in its bottom piece 40. The pin 64 extends into the slot 63 and contacts its sides. In turn, the pin 64 rigidly attaches to the circular disc 65 which may rotate about its center. Most of the back of the disc 65 has a flat configuration which lies against the back leg 29 of the Z bracket 23. The shaft 66, shown in FIG. 1, passes through the back leg 29 of the Z bracket 23 and rigidly adjoins the circular disc 65. In fact, the disc 65 and the shaft 66 may simply form part of a single piece.

Turning the shaft 66 thus has the effect of rotating the disc 65. Moreover, the knob 57, located on the outside of the back panel 11, attaches firmly to the shaft 66 to allow for the manual rotation of the latter.

The end of the shaft 67 closest to the disc 65 has screw threads formed on it. This allows for the attachment of the bolt 68 on the side of the bracket's leg 29 opposite the disc 65. The bolt 68 thus presses the washer 69 and 70 against one side of the leg 29 of the Z bracket 23 and holds the disc 65 against the other side of the leg 29. Consequently, the bolt 68 and the washer 70 keep the disc 65 pressed against the back leg 29 in the position shown in FIGS. 2 and 3.

Forming the washer 70 and the disc 65 of a low-friction material, such as Teflon ®, allows them to rotate relative to the back plate 29 although the bolt 68 firmly squeezes them against it. Rotate they must in order to move the holder 54 to the right and left which carries the casette from its insertion position to its operational position.

Specifically, after placing the casette between the plate 37 and the arms 38 and 39, the casette and, thus, the holder 54, must move to the right as seen in FIGS. 1 through 3. To accomplish this, the operator turns the knob 67 to the right (in FIG. 1). This rotates the shaft 66 in the same direction and results in a clockwise rotation of the disc 65.

As the disc 65 begins to rotate, the pin 64 moves initially towards the top of the slot 63. However, the rotation of the disc 65 causes it to contact and bear against the right side of the slot 63. Further clockwise rotation of the disc 65 forces the pin 64 to push against the right side of the slot 63 and move the holder 54 to the right.

During the first half of the journey of the holder 54 from the position of FIG. 2 to that in FIG. 3, the pin 64 moves towards the top of the slot 63 and very nearly reaches it. During the second half of the journey, the pin 64 continues to move to the right. However, it now travels downward in the slot 63. At the end of the journey, the pin 64 has moved the holder 54 to the position shown in FIG. 3. Once again, however, it has a location at the bottom of the slot 63.

Removing the casette from the controller 10 reverses the process which places the casette in its operational position described above. First, the attendant rotates the knob 67 to the left in FIG. 1. This induces a counterclockwise rotation of the disc 65. The pin 64, attached to the disc 65, begins to rise in the slot 63. It also contacts the left side of the slot 63 and moves the holder 54 to the left. For a while, the pin 64 continues to rise in the slot 63 while it moves the holder 54 to the left. Subsequently, however, the pin 64 descends in the slot 63 until the holder 54 has reached the left position. When the holder 54 returns to the position shown in FIGS. 1 and 2, the attendant may again disengage the casette and the controller from each other.

Since the pin 64 has a rigid attachment to the disc 65, it travels over the circumference of a circle as it moves between the positions of FIGS. 2 and 3. To allow for this required motion of the pin 64, the slot 63 must have a length equal to the radius of that circle plus, of course, the width of the pin 64 itself.

When the casette occupies its operational position within the controller 10, the metal holder 54 and, thus, the pin 64, occupy the position shown in FIG. 3. Specifically, the pin 64 lies as far to the right at the disc 65 can move it. Alternatively, if the slot 63 had its bottom located slightly below the configuration shown in the figures, the pin 64 would actually lie somewhat below its position in FIG. 3. In either case, to disengage the casette from the controller, the pin 64 initially moves upward and has no component of motion to the left. Subsequently, of course, it does move to the left.

However, physically pushing the pin 64 to the left, when in the position in FIG. 3, cannot cause it to rotate in the counterclockwise direction. Only an upward force can begin the movement of the pin 64 along its arc and, thus, produce counterclockwise rotation of the disc 65.

In particular, if the holder 54 attempted to push the pin 64 to the left in FIG. 3, it could not effect any motion of the pin 64 or the disc 65. Moreover, when a casette sits in the holder 54, pushing the casette to the left cannot move the pin 64 or rotate the disc 65 in the direction that would disengage the casette from the controller 10.

The pin 64 and the disc 65 prevent motion of the casette to the left which represents the direction it must move to disengage from the controller 10. Consequently, the pin 64 and the slot 63 lock the holder 54 and, thus, the casette in a position in which the controller 10 can effectively operate the inlet and outlet valves on the casette. The pin 64 and the disc 65 prevent disengagement of the casette from the controller 10 due to an inadvertant force, such as from an accidental knocking.

Similarly but less importantly, pin 64 in FIG. 2 can only move upwards in order for the holder 54 to move to the right. An accidental force applied against the holder 54 or against the casette retained in the holder 54 cannot cause movement of the casette toward the engagement position. The locking of the bracket to the left of FIG. 2 does provide a benefit, however. After the removal of the casette from the holder 54, the holder 54 remains properly aligned with the opening 31 in the front panel 15. There, it can readily receive the insertion of a subsequent casette.

After a casette enters between the plate 37 and the arms 38 and 39 in FIGS. 1 and 2, it receives transportation to the right until the holder 54 has the position shown in FIG. 3. With the holder 54 in this configuration, a casette 75 will occupy its operational position as in FIG. 4.

The casette 75 includes the base section of plastic 76 and the plastic cover slip 77. Fused together, they hold the elastomeric membrane 78 between them. The cover slip 77 has the protuberance 81 which barely fits between the upper arm 38 and the lower arm 39 to roughly align the casette 75 in the controller 10. In order to provide a fine adjustment of the casette 75, the controller 10 includes the alignment pins 57 and 58 attached to the middle leg 84 of the Z bracket 23.

Normally, the plastic cover slip 77 occupies a position between the base plastic section 76 and the middle leg 84. However, the base plastic section 76 includes the circular protuberances 85 and 86 which actually extend through openings 87 and 88, respectively, in the cover slip 77. The protuberances 85 and 86 have the depressions 89 and 90 formed in them. To closely align the casette 75 and the controller 10, the alignment pins 57 and 58 fit into the depressions 89 and 90.

The pins 57 and 58, thus, directly provide substantially no alignment of the cover section 77 although it normally sits between the base plastic section 76 and the middle leg 84. However, the openings 87 and 88 in the cover slip 77 surround the protuberances 85 and 86. This produces the necessary alignment of the cover slip 77 to both the base section of plastic 76 and the controller 10.

A critical alignment, of course, exists between the base plastic section 76 and the valve members 59 and 60. The valve members 59 and 60 must properly sit upon the inlet valve face 93 and the outlet valve face 94, respectively, to control the amount of fluid passing through the casette 75. The valve seats 93 and 94, however, form part of the base section of plastic 76. Its proper alignment results directly from the insertion of the alignment pins 57 and 58 into the openings 89 and 90 which also form part of the base plastic section 76.

Alternatively, the alignment pins 57 and 58 could snugly fit into appropriately sized depressions in the cover section 77. However, the correct alignment of the valve members 59 and 60 relative to the valve seats 93 and 94 would then depend upon the orientation of the cover slip 77 to the base plastic section 76. The direct insertion of the pins 57 and 58 into the openings 89 and 90 in the base section 76 eliminates the need for an absolutely precise alignment between the base section 76 and the cover slip 77.

The valve members 59 and 60 must, nonetheless, move through the openings 97 and 98 in the cover slip 77. Making the openings 97 and 98 appreciably larger than needed for the valving members 59 and 60 eliminates the criticality of the alignment of the cover slip 77 to either the base section 76 or to the controller 10.

FIG. 4 shows a close fit between the alignment pin 57 and the opening 89. At the other end of the drawing, however, the pin 58 appears to have a loose fit within the opening 90. In fact, the opening 90 has an oblong shape which allows motion in its inside of the pin 58 in the direction towards and away the opening 89 at the casette's other end. The opening 90, however, fits close to the pin 58 in the direction into and out of the paper. When the pin 57 sits in the opening 89, the only allowed motion of the casette 75 relative to the controller 10 involve a rotation around the pin 57. The close fit of the opening 90 to the front and back of the pin 58, as seen in FIG. 4, specifically prevents this type of motion. Thus, the looseness of the oblong opening 90 does not detract from the precise alignment of the casette 75 in the controller 10. It merely eliminates the criticality of the distance of the pin 58 away from the pin 57.

Similarly, the opening 87 in the cover slip 76 tightly fits around the circular protuberance 85 of the basic plastic section 76. At the other end, the cover section 76 has an oblong opening 88 which allows some leeway to the circular protuberance 86. Again, the sides of the sides of the oblong opening 88 closely approach the protuberance 86. No misalignment between the two sections of plastic can result. It merely lowers the exactness with which the manufacturing process must locate the opening 88 relative to the protuberance 86.

The controller 10 and the casette 75 operate cyclicly. The cycle of operation begins with the closing of the outlet port 101. This occurs when the outlet valve member forces the membrane 78 to seat upon the outlet valve face 94. Retracting the inlet valve member 59 allows the membrane 78 to contract to the configuration shown in FIG. 4. This opens the inlet port 102.

Fluid may then flow from the inlet channel 103 through the inlet port 102. It arrives at the metering chamber 103 located between the membrane 78 and the portion 104 of the base section 76 located between the inlet and outlet ports 102 and 101, respectively.

As the fluid enters the metering chamber 103, the membrane 78 expands until it contacts the concave depression formed in the cover plastic section 77. At this point, the membrane 78 can expand no further and, consequently, the metering chamber 103 has reached its maximum volume. The slot 107 in the cover plastic section 77 allows for the equalization of the air pressure between the cover section 77 and the membrane 78.

FIG. 5 shows the configuration of the membrane 78 in the region of the outlet port 101 when the valve member 60 has closed it. As shown there, the valve member 60 has extended towards the outlet valve face 94. When it moves in that direction, it contacts the membrane 78, stretches it, and forces it to seat tightly upon the valve face 94. With the membrane 78 seated upon the face 94, no fluid can pass out the outlet port 101.

To continue the cycle of operation, the controller inserts the inlet valve 59 until it stretches the membrane 78 sufficiently to seat upon the valve face 93 of the inlet port 102. Then, the controller retracts the outlet valve member 60 which allows for the contraction of the membrane 78 in the region of the outlet port 101. As the membrane 78 there contacts, it moves away from the outlet valve face 94 which, thus, opens the outlet port 101. With the outlet port 101 open, the fluid from the metering chamber 104 may pass through the outlet port 101, the outlet channel 110, and to the patient.

The controller completes the cycle of operation by again inserting the outlet valve member 60 to cause the membrane 78 to close the outlet port 101. When all of the fluid from the metering chamber 104 has passed out of the casette 75, the middle portion of the membrane 78 contracts to the flat position shown in FIG. 4.

To move the valving members 59 and 60, the controller 10 includes the E-frame electromagnet, shown generally at 117 in FIGS. 1 to 3. Screws and posts 119 attach the electromagnet 117 to the front leg 25 of the Z-shaped bracket 23.

As seen in FIGS. 2 and 3, the electromagnet 117 includes the coil 118 which surrounds the magnet's middle leg 119. The back 120 of the magnet 117 connects its middle leg 119 to its side legs 120 and 121.

When current flows along the leads 122 to the magnet 117, it induces the ends of both the legs 120 and 121 to become magnetic poles of the same type. Thus, the side legs 120 and 121 may both have a North pole at their ends. Reversing the current in the leads 122 causes the opposite magnetic pole to appear at the ends of the legs 120 and 121. Following the example given above, reversing the current in the leads 122 produces a South magnetic pole at the ends of the legs 120 and 121.

Adjacent to the end of the leg 120 sits the permanent magnet 125, while the permanent magnet 126 has a location in proximity to the end of the other side leg 122. Both of the permanent magnets 125 and 126 connect to the same rocker arm 127. However, the magnets 125 and 126 present opposite magnetic poles to the E-frame electromagnet 117. In other words, if the permanent magnet 125 has its North pole lying closest to the end of the side leg 120, then the permanent magnet 126 has its South pole lying closest to the end of the side leg 121.

As stated above, the current passing along the leads 122 and through the coil 118 can cause the ends of both side legs 120 and 121 to become South magnetic poles. When that occurs, the South magnetic pole on the side leg 120 attracts the North magnetic pole on the permanent magnet 125. Simultaneously, the South magnetic pole on the leg 121 repels the South pole on the permanent magent 126 to produce the configuration shown in FIG. 2.

Reversing the direction of the current in the leads 122 and the coil 118 produces the opposite effect, or North magnetic poles at the ends of the side legs 120 and 121. In this instance, the resulting North magnetic pole on the side leg 120 repels the North magnetic pole of the permanent magnet 125. Further, the North magnetic pole on the side leg 121 attracts the South magnetic pole on the permanent magnet 126. This reversal of attraction and repulsion causes the rocker arm 127 to rotate about its pivot point 128 located on a line passing through the center leg 119 of the E-frame electromagnet 117. The rocker arm 127 will continue to rotate until the permanent magnet 126 makes actual contact with the side leg 121 and produces the configuration shown in FIG. 3.

In general, the rotating of the rocker arm 127 about its pivot point 128 moves the valve members 59 and 60 to open and close the inlet and the outlet valves on the casette 75. To provide the interconnection between the rocker arm 127 and the valve members 59 and 60, the spring member 131 attaches to the former with the aid of the screw 132. Additional screws at the pivot point 128 attach the side 133 of the spring member 131 to the middle leg 119 electromagnet 117. The spring member 131 in turn has the two legs 135 and 136. Each of the legs 135 and 136 has a slot in its end barely large enough to allow it to fit into grooves provided near the end of the movable valve member 59 and 60, respectively. The end of the valve members 59 and 60 with these grooves lie on the same side of the middle leg 84 of the Z bracket 23 as the rocker arm 127. FIG. 1 shows the slot in the leg 135 with barely sufficient room to enter the groove in the end of the inlet valve member 59.

As the rocker arm rotates about the pivot point 128 between the two positions shown in FIGS. 2 and 3, the spring member 131 rotates between its two positions, which also appear in those figures. In the position in FIG. 2, the leg 136 of the connecting member 131 lies closer to the middle plate 84 and thus to the casette that the holder 54 would retain. This situation, in particular, receives illustration in FIG. 4. The leg 136 thus projects the outlet valve member sufficiently far through the plate 84 to cause the membrane 78 to close off the outlet port 101. The other leg 135 of the spring member 131 retracts the inlet valve member 59 which, in turn, opens the inlet port 102.

When the connecting member changes its position from that of FIG. 2 to that in FIG. 3, the opposite result occurs. Specifically, it thrusts the inlet valve member 59 through the middle plate 84 to close the inlet valve. It then retracts the outlet valve member 60 sufficiently to allow the casette's outlet 101 to open.

The composition of the spring member 131 should provide it with a modicum of inherent resiliency or "springiness". Moreover, it should have a location sufficiently close to the middle plate 84 that a leg 135 or 136 must flex when forcing a valve member, 59 or 60, respectively, to close its appropriate valve in the casette. As a result, when the rocker arm 127 changes positions, the spring member causes the other valve member to start moving and close off its valve in the casette. The other leg, during this time, starts to unbend, but keeps its valve member in the position where its valve stays closed.

Thus, the spring member 131, with the flexing legs 132 and 133 and a close location to the middle plate 84, when it changes its position, causes the open valve to close before it allows the closed valve to open. This prevents a period of time during which both valves in the casette could open and permit an unknown amount of fluid to pass to the patient.

If no current flows along the leads 122 to the coil 118, no magnetic pole will appear at the end of either the side legs 120 or 121. However, the permanent magnetic poles 125 and 126 still remain. Both of these would then exert an attractive force upon the ferromagnetic material of the side legs 120 and 121. The pole creating the greater force would move to and actually contact the leg nearest it while the other pole would then move from its leg. However, the permanent magnetic poles 125 and 126 have very nearly the same strength. Thus, the pole lying closer to the E-frame would actually move towards its leg. Accordingly, with no current in the electromagnet 117, a magnetic bistable device results; either the permanent pole 125 makes contact with the E-frame to create the configuration shown in FIG. 2. Or, the magnetic pole 126 would attract itself to the bottom leg 121 to produce the situation in FIG. 3. One of these two situations must result because of the bistable magnetic device created by the permanent magnets 125 and 126 in proximity to the electromagnet 117 without any current in it.

Moreover, each of the situations in FIGS. 2 and 3 place one of the movable valve members 59 or 60 in a position where it closes its valve in the casette. In FIG. 2, the outlet would close will, in FIG. 3, the inlet would close. Thus, one of the valves in the casette would necessarily have to close as long as the casette remained engaged in the controller 10. This occurs even if no current passed to the electromagnet 117. Under no circumstances would the controller 10 allow fluid to pass in an uncontrolled manner to the patient.

In the figures, the magnetic bistable device includes the ferromagnetic material of the electromagnetic 117. Other powering devices, however, could move the rocker arm 127. Examples include mechanical or pneumatic motive means. Nonetheless, placing ferromagnetic material in the locations of the side legs 120 and 121 and permanent magnets 125 and 126 on the rocker arm 127 would still produce the magnetic bistable device. This would continue to assure the closure of at least one valve in a casette placed in the controller 10.

When using the electromagnet 117, the rocker arm 127 with its pivot point 128 should not make direct contact with the middle leg 119 of the electromagnet 117. If it did contact, it could provide a shunt for the magnetic field through the middle leg 119 of the electromagnet 117. The shunt would provide a circuit between the permanent magnet making actual contact with a side leg. The shunt would reduce the field strength of the other side leg which repels the other permanent magnet. Moreover, displacing the rocker arm 127 slightly from the middle leg 119 of the electromagnet 117 prevents the grinding of the two components and the concomitant production of coarse fillings between them which could interfere with the free rotation of the rocker arm 127.

Instead of having the two attached permanent magnets 125 and 126, the rocker arm 127 may simply take the form of a long permanent magnet having its poles near the location of the magnets 125 and 126. That would assure the rocker arm 127 of magnetic poles of equal strength. Moreover, such a permanent magnet could not have an induced pole at its middle. Consequently, the magnetic field could not shunt across the middle of the rocker arm 127 to the middle leg 119 of the electromagnet 117. However, the rocker arm 127 should still remain slightly removed from the middle leg 119. This prevents the grinding of the two together as the rocker arm 127 rotates and the production of filings from either component to interfere with the free rotation of the rocker arm 127.

Figure 7:
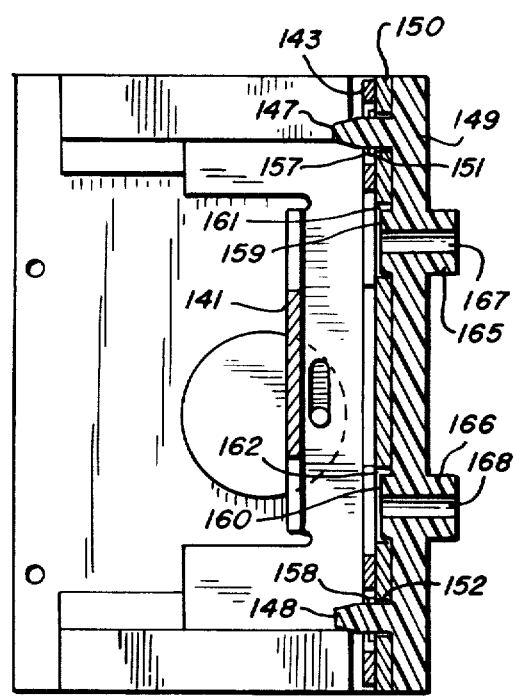
FIG. 7 has a cross-sectional view, along the line 7—7, of the structural member of FIG. 6.

FIG. 6 shows a metal holder 41 with arms 143 and 144 slightly different from the arms 38 and 39 of the prior figures. The openings 145 and 146 in the arms 143 and 144, respectively, allow the alignment pins 147 and 148 to pass through and reach the casette 75. As shown in FIG. 7, the alignment pins 147 and 148 form part of an alignment block 149 which sits behind the middle leg 150 of a Z bracket corresponding to the bracket 23 of FIG. 1. The bracket's middle leg 150 has the similar openings 151 and 152 through it. These again allow the alignment pins 147 and 148 to reach the casette.

The snap rings 157 and 158 clamp on to the alignment pins 147 and 148. They affix the alignment block 149 to the Z bracket's middle leg 150.

The alignment block 149 also has the protuberances 159 and 160 oriented in the same direction as the alignment pins 147 and 148. The middle leg 150 has the openings 161 and 162 into which fit the protuberances 159 and 160.

The other side of the mounting block 150 has the protuberances 165 and 166. These generally fall at the same location as the protuberances 159 and 160, but on the other side. The opening 167 passes through the mounting block 149 and centers itself in the proturberances 159 and 165. The second opening 168 also passes through the alignment block 159 and has a central location in the protuberances 160 and 166.

The openings 167 and 168 serve a dual purpose. First, they guide the valving members 59 and 60 to their proper locations relative to the inlet 102 and the outlet 101 on the casette 75. Secondly, the alignment block 149 has a composition of a low frictional material. Delrin 500 CL ®, an acetal resin manufactured by the E. I. du Pont de Nemours & Co., represents a good example of such a material. Its surface has a low coefficient of friction.

The valving members 59 and 60 protract and retract to operate the valves on the casette. Sliding on the material of the alignment block 149, they encounter substantially no frictional resistance from the surfaces of the openings 167 and 168.

Figure 8:
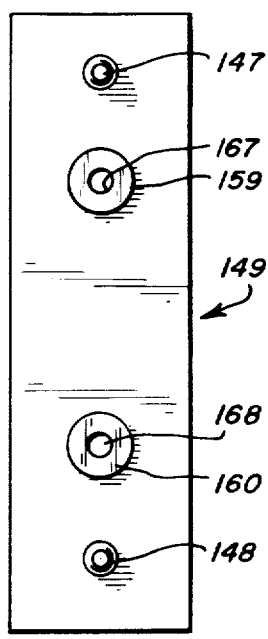
FIG. 8 gives a front elevational view of an alignment block which includes components for orientating the casette in the controller and guiding the controller's valving members.

FIG. 8 shows the front of the alignment block 149 prior to its assembly on the Z bracket's middle leg 150. This surface shows the alignment pins 147 and 148, the protuberances 159 and 160, and the openings 167 and 168.

Figure 9:
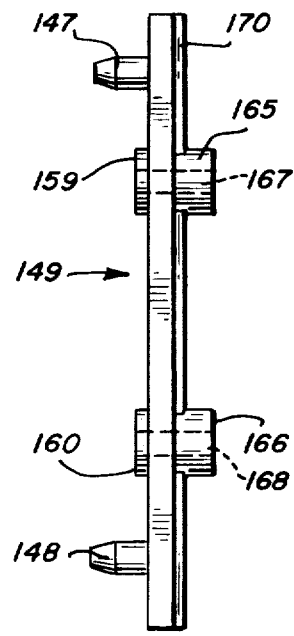
FIG. 9 gives a side elevational view of the alignment block of FIG. 8.
Figure 10:
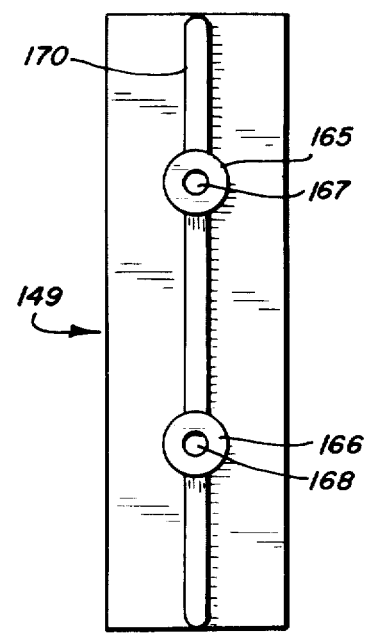
FIG. 10 gives a rear elevational view of the alignment block of FIGS. 8 and 9.

The side view of FIG. 9 shows these components as well as the protuberances 165 and 166 on the side of the alignment block 149 opposite to the protuberances 159 and 160. The openings 167 and 168 through these protuberances appear in phantom in the figure. FIG. 9 also shows a small ridge 170 on the back of the alignment block 149. The ridge 170 provides the alignment block 149 with greater structural rigidity. FIG. 10 shows the ridge 170 passing down the middle of the back of the alignment block 149.

As suggested above, the alignment pins 147 and 148 provide the fine alignment of the casette 75 within the controller 10. The openings 167 and 168 guide the valving members 59 and 60 as they operate the openings 101 and 102 in the casette 75. Consequently, the same section of material that aligns the casette also guides the valve members.

The alignment pins 147 and 148 do not attach to a separate section of material which then either guides the valve members or would include further sections of material to perform that function. The resulting alignment would then not only depend upon the orientation of the casette relative to the alignment pins 147 and 148. The casette's proper placement would also depend upon the correct orientation of the pins 147 and 148 to, for example, the Z bracket's middle leg 150. Utilizing the single molded block 149 assures the correct orientation of the alignment pins 147 and 148 to the guiding openings 167 and 168.

Accordingly, what is claimed is:

1. An apparatus for delivering controlled amounts of fluid through a flow path, which comprises: a separate casette defining said flow path, said casette defining metering means for holding a predetermined volume of fluid; closable inlet means in fluid communication with said metering means for permitting the flow of a fluid into said metering means; and closable outlet means in fluid communication with said metering means for permitting the flow of a fluid out of said metering means; and a controller adapted to receive said casette, having inlet-controlling means for closing said inlet means and outlet-controlling means for closing said outlet means and first means for receiving and holding said casette at a position remote from said inlet and outlet controlling means, and second means for moving said casette into engagement with said inlet and outlet controlling means, said means for moving the casette into engagement with the inlet and outlet controlling means comprising transporting means which includes (i) a pin rotatable in a path defining half the circumference of a circle, and (ii) a slot defined in the said means for receiving and holding said casette; said slot being positioned in a direction normal to the direction of motion of said casette into engagement with the inlet and outlet controlling means, whereby upon rotation of said pin through the half circumferential path, said pin moves from one end to the other of the slot and at the same time moves said means for receiving and holding said casette in a direction generally parallel to the diameter between the ends of said half circumferential path.

2. The improvement of claim 1 wherein said inlet-controlling means includes a first elongated member movable along a first straight line, said outlet-controlling means includes a second elongated member movable along a second straight line parallel to said first straight line, and where said receiving and holding means, when engaged with said casette, places said inlet means on said first line and said outlet means on said second line.

3. The improvement of claim 2 wherein said inlet means, said outlet means, and said metering means are each formed, in part, from a section of substantially rigid material and, in part, from a flexible membrane; said membrane being substantially enclosed between a first section of rigid material and a second section of rigid material rigidly affixed to said first section of rigid material; said first and second elongated members move through said second section of rigid material to close off said inlet and said outlet means, respectively; and said first positioning means includes a first part coupled to said controller and a second part formed integrally with said first section of rigid material, said first and second parts contacting each other to orient said inlet means and said outlet means relative to said inlet-controlling means and said outlet-controlling means, respectively.

4. The improvement of claim 3 wherein said first elongated member, to close said inlet means, moves towards said first section of rigid material and stretches said membrane in the region of said inlet means to seal off said inlet means and prevent the passage of fluid therethrough into said metering means, and said second elongated member, to close said outlet means, moves towards said first section of rigid material and stretches said membrane in the region of said outlet means to seal off said outlet means and prevent the passage of fluid therethrough from said metering means.

5. The improvement of claim 4 wherein said second means includes means to limit the travel of said casette towards said elongated members.

6. The improvement of claim 1 wherein said inlet-controlling means includes a first elongated member movable along a first straight line, said outlet-controlling means includes a second elongated member movable along a second straight line parallel to said first straight line, and where said receiving and holding means, when engaged with said casette, places said inlet means on said first line and said outlet means on said second line.

7. The improvement of claim 6 wherein said inlet means, said outlet means, and said metering means are each formed, in part, from a section of substantially rigid material and, in part, from a flexible membrane; said membrane is substantially enclosed between said first section of rigid material and a second section of rigid material rigidly affixed to said first section of rigid material; said first and second elongated members move through said second section of rigid material to close off said inlet and said outlet means, respectively; and said first positioning means includes a first part coupled to said controller and a second part formed integrally with said first section of rigid material, said first and second parts contacting each other to orient said inlet means and said outlet means relative to said inlet-controlling means and said outlet-controlling means, respectively.

8. The improvement in accordance with claim 7 wherein said means for moving the casette into engagement with the inlet and outlet controlling means also includes locking means for holding said casette in said engagement, to prevent motion of said casette away from said elongated members.

9. The improvement of claim 8 wherein said first elongated member, to close said inlet means, moves towards said first section of rigid material and stretches said membrane in the region of said inlet means to seal off said inlet means and prevent the passage of fluid therethrough into said metering means, and said second elongated member, to close said outlet means, moves towards said first section of rigid material and stretches said membrane in the region of said outlet means to seal off said outlet means and prevent the passage of fluid therethrough from said metering means.

10. The improvement of claim 1 which includes positioning means spatially removed from said inlet and outlet controlling means, for precisely orienting said casette to cause the inlet and outlet means to be engagable with the inlet and outlet controlling means.

11. The improvement in accordance with claim 10 in which said positioning means includes first and second indentations defined in said casette and first and second protruberances attached to said controller, with said first protruberance being adapted to fit snugly inside of said first indentation and said second protruberance being adapted to fit inside said second indentation when the casette is in engagement with the inlet and outlet controlling means, to prevent rotation of said casette.

12. The improvement in accordance with claim 11 in which said first means for receiving and holding the casette at a position remote from the inlet controlling means includes first and second rigid members connected together, and adapted to receive said casette between said rigid members; said casette defining at least one ridge to engage one of said rigid members for alignment in orientation of the casette in a predetermined position.

13. The improvement in accordance with claim 1 in which said casette is formed in part from a rigid housing, said inlet and outlet means each including an aperture in said housing, and a section of flexible material retained against said aperture within said rigid housing, whereby each flexible material may be pressed against said aperture for sealing, said controller means defining said first and second rigid members adapted for association with said inlet and outlet means for pressing said flexible material against the aperture.

14. The improvement in accordance with claim 13 having means for locking said casette into engagement with the inlet and outlet controlling means, selectively preventing said means for moving the casette with a linear force.

15. The improvement of claim 13 wherein said moving means includes a rotatable shaft having its center at the origin of said circular arc, and rigidly coupled to said pin.

16. The improvement in accordance with claim 15 in which said inlet-controlling means and outlet-controlling means are in turn controlled by bi-stable magnetic means for holding, in the absence of power, one or the other of the inlet controlling means and outlet controlling means in a position to close said inlet or outlet means.

17. The improvement of claim 16 wherein the inlet-controlling means includes a first elongated member movable along a first straight line, said outlet-controlling means includes a second elongated member movable along a second straight line parallel to said first straight line, and where said receiving and holding means, when engaged with said casette, places said inlet means on a first line and said outlet means on said second line.

18. An apparatus for delivering controlled amounts of fluid through a flow path, which comprises: a separate casette defining said flow path, said casette defining metering means for holding a predetermined volume of fluid; closable inlet means in fluid communication with said metering means for permitting the flow of fluid into said metering means; and closable outlet means in fluid communication with said metering means for permitting the flow of a fluid out of said metering means; and a controller adapted to receive said casette, having inlet-controlling means for closing said inlet means and outlet-controlling means for closing said outlet means, and further including first means for receiving and holding said casette at a position remote from said inlet and outlet controlling means, and second means for moving said casette into engagement with said inlet and outlet controlling means, the improvement comprising: positioning means including first and second indentations defined in said casette, and first and second protruberances attached to said controller and adapted to fit inside said first and second indentations in which said first protruberance passes through a first, relatively tight-fitting aperture in said casette while said second protruberance passes through an aperture in said casette which is of generally oblong shape to allow the second protruberance an amount of fitting tolerance, the longest axis of said oblong aperture being directed toward the first aperture.

19. The improvement of claim 18 wherein said second means includes (i) a pin movable over 180° of the circumference of a circle and (ii) a slot inside of which said pin fits, said slot having a length approximately equal to the radius of said circle, said pin, when at either end of said 180° arc, lying at one end of said slot and, when in the middle of said 180° arc, lying at the other end of said slot, said ends of said 180° arc determining a straight line lying parallel to said first and second straight lines.

20. The improvement of claim 19 wherein said transporting means includes actuating means for manually moving said pin to any position in said 180° arc.

21. A fluid-flow limiting combination having:
(a) a casette with:
(1) metering means for holding a predetermined volume of a fluid;
(2) closable inlet means in fluid communication with said metering means for permitting the flow of a fluid into said metering means; and
(3) closable outlet means in fluid communication with said metering means for permitting the flow of a fluid out of said metering means; and
(b) a controller having:
(1) inlet-controlling means for closing said inlet means;
(2) outlet-controlling means closing said outlet means; the improvement comprising:
(3) transporting means for moving said casette between a first position and a second position, said first position being closer to said inlet-controlling means and said outlet-controlling means than said second position, said transporting means including a pin movable over an arc constituting essentially half of the circumference of a circle, said pin being retained within an elongated slot of a movable frame for carrying said casette, said slot defining a length at least about equal to the radius of said circle, the elongated dimension of said slot remaining substantially perpendicular to the direction said casette moves between said first position and said second position, said pin, when said casette is in said first position, being at a first end of said arc and one end of said slot, said pin moving to the second end of said arc as said casette moves from said first position toward said second position, said pin, when leaving said first end of said arc to move toward the second end of the arc, moving in a direction parallel to said elongated dimension of said slot; locking means coupled to said transporting means for, when said casette is in said first position, selectively preventing the movement of said casette toward said second position upon the application to said casette of a linear force in the direction said casette travels when moving from said first position toward said second position.

22. The improvement of claim 21 wherein said pin, when leaving said first end of said arc to move towards said second end of said arc, can move at least some distance over said arc without said casette moving relative to said controller.

23. The improvement of claim 22 wherein said transporting means includes a turning shaft having a center at the center of said circle and rigidly coupled to said pin, said controller further including grasping means for holding said casette, said grasping means being coupled to said slot, and the motion of said pin in a direction perpendicular to the elongated direction of said slot moving said slot and said grasping means in said perpendicular direction.

24. The improvement of claim 23 wherein said arc constitutes half of said circle, and the length of said slot is equal to the radius of said circle plus the width of said pin.

25. The improvement of claim 24 wherein said locking means, when said casette is in said second position, selectively prevents the movement of said casette towards said first position upon the application to said casette of a linear force in the direction said casette travels when moving from said second position towards said first position.

26. In a controller for use with a casette having:
(1) metering means for holding a predetermined volume of a fluid;
(2) closable inlet means in fluid communication with said metering means for permitting the flow of a fluid into said metering means; and
(3) closable outlet means in fluid communication with said metering means for permitting the flow of a fluid out of said metering means;
said controller having:
(1) inlet-controlling means for closing said inlet means;
(2) outlet-controlling means closing said outlet means; the improvement comprising:
(3) transporting means for moving said casette between a first position and a second position, said first position being closer to said inlet-controlling means and said outlet-controlling means than said second position, said transporting means including a pin movable over an arc constituting essentially half of the circumference of a circle, said pin being retained within an elongated slot of a movable frame for carrying said casette, said slot defining a length at least about equal to the radius of said circle, the elongated dimension of said slot remaining substantially perpendicular to the direction said casette moves between said first position and said second position, said pin, when said casette is in said first position, being at a first end of said arc and one end of said slot, said pin moving to the second end of said arc as said casette moves from said first position toward said second position, said pin, when leaving said first end of said arc to move toward the second end of the arc, moving in a direction parallel to said elongated dimension of said slot; locking means coupled to said transporting means for, when said casette is in said first position, selectively preventing the movement of said casette toward said second position upon the application to said casette of a linear force in the direction said casette travels when moving from said first position toward said second position.

27. The improvement of claim 26 wherein said transporting means includes a turning shaft having a center at the center of said circle and rigidly coupled to said pin, said controller further including grasping means for holding said casette, said grasping means being coupled to said slot, and the motion of said pin in a direction perpendicular to the elongated direction of said slot moving said slot and said grasping means in said perpendicular direction.

28. The improvement of claim 27 wherein said arc constitutes half of said circle, and the length of said slot is equal to the radius of said circle plus the width of said pin.

29. The improvement of claim 28 wherein said locking means, when said casette is in said second position, selectively prevents the movement of said casette towards said first position upon the application to said casette of a linear force in the direction said casette travels when moving from said second position towards said first position.

30. An alignment block comprising:
(a) a section of substantially rigid material;
(b) affixing means, coupled to said section, for affixing said section to a substantially flat plate having an opening therethrough in a position at a location where said section covers substantially all of said opening through said plate;
(c) guide means, coupled to said section and including at least one opening therethrough, said opening through said guide means, when said attaching means affixes said section to said plate in said position, being located at said opening through said plate, for guiding an elongated member through said opening through said section; and
(d) alignment means, coupled to said section, for orienting an object relative to said guide means.

31. The block of claim 37 wherein said alignment means includes at least one protuberance coupled to and extending from said section.

32. The block of claim 38 wherein said section, said guide means, and said alignment means are formed integrally.

33. The block of claim 39 wherein said guide means is formed from a material having a low coefficient of friction.

34. The block of claim 40 wherein said material has a low coefficient of friction is a plastic.

35. The block of claim 41 wherein said alignment means includes two protuberances having a spacing between them.

36. The block of claim 42 wherein said protuberances form part of said attaching means.

37. The block of claim 42 wherein said guide means includes two openings through said section.

38. The block of claim 44 wherein said attaching means affixes said section to said plate at a location where each of said openings through said section is adjacent to an opening through said plate.

39. In a fluid-flow limiting combination having:
(a) a casette with:
(1) metering means for holding a predetermined volume of fluid;
(2) closable inlet means, in fluid communication with said metering means, for permitting the flow of fluid into said metering means; and
(3) closable outlet means, in fluid communication with said metering means, for permitting the flow of fluid out of said metering means; and
(b) a controller with:
(1) first rigid member means, movable between a first position and a second position, for, when in said second position, closing said inlet means;
(2) second rigid member means, movable between a third position and a fourth position, for, when in said fourth position, closing said outlet means;
(3) moving means, connectable to and operatable upon a source of power and coupled to said first member means and said second means, for selectively moving said first member means to said second position to close said inlet means or moving said second member means to said fourth position to close said outlet means; and
(4) structural means, coupled to said moving means, said first member means, and said second member means, for orientating said moving means, said first member means, said second member means, relative to each other,
the improvement wherein said structural means includes:
(A) a substantially flat plate having a opening therethrough and connected to said moving means;
(B) a section of substantially rigid material;
(C) affixing means, coupled to said section, for affixing said section to said substantially flat plate in a position at a location where said section covers substantially all of said opening through said plate;
(D) guide means, coupled to said section and including at least one opening therethrough, said opening through said guide means, when said attaching means affixes said section to said plate in said position, being located at said opening through said plate, for guiding said first and said second member means through said opening through said plate; and
(E) alignment means, coupled to said section, for orienting said casette relative to said guide means.

40. The improvement of claim 46 wherein said alignment means includes at least one protuberance coupled to and extending from said section and said casette includes at least one identation formed therein and of a size to snugly fit around said protuberance.

41. The improvement of claim 47 wherein said section, said guide means, and said alignment means are formed integrally.

42. The improvement of claim 48 wherein said guide means is formed from a material having a low coefficient of friction.

43. The improvement of claim 49 wherein said material is a plastic.

44. The improvement of claim 49 wherein said alignment means includes two protuberances having a spacing between them and said casette has two indentations having said spacing between them.

45. The improvement of claim 51 wherein (i) said guide means includes two openings through said section, (ii) said first member means is a first elongated member snugly fitting into one of said openings through said section, (iii) said second member means is a second elongated member snugly fitting through the other of said openings through said section, and (iv) said two openings through said section have a distance between them and said inlet means and said outlet means have said distance between them.

46. In a controller member for use with a casette for delivering controlled amounts of fluid through a flow path through the casette, said casette defining closable inlet and outlet means and metering means therebetween for holding a predetermined amount of fluid, the controller defining inlet-controlling means for closing the inlet means and outlet controlling means for closing the outlet means; first means for receiving and holding said casette in a position remote from the inlet and outlet controlling means, and second means for moving said casette into engagement with said inlet and outlet controlling means, said means for moving the casette into engagement with the inlet and outlet controlling means comprising transporting means which includes (i) a pin rotatable in a path defining half the circumference of a circle, and (ii) a slot defined in said means for receiving and holding said casette; said slot being positioned in a direction normal to the direction of motion of said casette into engagement with the inlet and outlet controlling means, whereby upon rotation of said pin through the half circumferential path, said pin moves from one end to the other of the slot and at the same time moves said means for receiving and holding said casette in a direction generally parallel to the diameter between the ends of said half circumferential path.

* * * * *